(12) United States Patent
McEllen

(10) Patent No.: US 7,879,299 B2
(45) Date of Patent: Feb. 1, 2011

(54) PADDLE FAN MEDALLION FOR ENHANCEMENT OF ROOM AIR QUALITY

(76) Inventor: John J. McEllen, 17293 Bittersweet Trail, Chagrin Falls, OH (US) 44023

( * ) Notice: Subject to any disclaimer, the term of this patent is extended or adjusted under 35 U.S.C. 154(b) by 0 days.

(21) Appl. No.: 12/215,303

(22) Filed: Jun. 26, 2008

(65) Prior Publication Data

US 2009/0035177 A1  Feb. 5, 2009

Related U.S. Application Data

(60) Provisional application No. 60/929,418, filed on Jun. 26, 2007.

(51) Int. Cl.
*A61L 9/00* (2006.01)
(52) U.S. Cl. .................. 422/305; 422/120; 422/124
(58) Field of Classification Search .................. 422/24, 422/120, 124, 305
See application file for complete search history.

(56) References Cited

U.S. PATENT DOCUMENTS

| 3,235,325 | A | * | 2/1966 | Storchheim | 96/224 |
|---|---|---|---|---|---|
| 5,195,870 | A | * | 3/1993 | Liu | 415/5 |
| 5,349,513 | A | * | 9/1994 | Taylor, III | 362/404 |
| 6,019,577 | A | * | 2/2000 | Dye | 416/5 |
| 2005/0058584 | A1 | * | 3/2005 | Shyu | 422/305 |

* cited by examiner

*Primary Examiner*—Sean E Conley
(74) *Attorney, Agent, or Firm*—L. Lawton Rogers, III

(57) ABSTRACT

Accessories and methods for ceiling paddle fan fixtures for enhancing room air quality and killing common air borne viruses by air sterilization immediately within the room where the germs originate in a relatively large and diffuse sterilization zone at a relatively low UV radiation level through which a relatively high volume of air is circulated by a paddle fan.

18 Claims, 3 Drawing Sheets

PADDLE FAN MEDALLION FOR ENHANCEMENT OF ROOM AIR QUALITY

RELATED APPLICATIONS

Applicant claims the priority of Application Ser. No. 60/929,418 filed Jun. 26, 2007 the entire disclosure of which is herein incorporated by reference.

BACKGROUND OF THE INVENTION

The present invention relates to accessories and methods for ceiling paddle fan fixtures for enhancing room air quality and killing common air borne viruses such as influenza and rhinovirus (the common cold) which are very susceptible to UV-C irradiation. Bacteria and spores are also affected by UV-C but are rarely transmitted in air. However, tuberculosis bacteria is almost always transmitted in air and is very susceptible to UV-C.

A contagious person continually contaminates the air within the room by the act of breathing. This contaminated air is circulated within the room and throughout the building by the heating and air conditioning system and it is thus highly desirable to effect air sterilization immediately within the room where the germs originate so that others in the room or building are not exposed to germ concentration levels that could cause infection.

As disclosed in applicant's co-pending application Ser. No. 11/823,507 filed Jun. 28, 2007, the entire disclosure of which is hereby incorporated by reference herein, the use of short wave ultra violet ("UV-C") sources for the sterilization of air is well known. The usefulness of UV-C irradiation on air quality lies in the effect on germs (microorganisms) transmitted in aerosolized form. Such infectious germs are generally less than 0.3 microns in diameter and are suspended or "float" in the air. The infection problem is particularly acute in spaces with closed air conditioning systems such as airplanes and office buildings etc. Because of the need to conserve energy, even homes, shops and restaurants are limiting the addition of fresh air in air conditioning systems and are re-circulating air. The recirculation of air increases the probability of person-to-person transmissions. The problem is also particularly acute in hospitals, clinics and the like where infected people congregate for treatment.

Because of well known safety considerations, air sterilization products (e.g., in-duct, ceiling and portable tabletop and floor standing units) generally avoid emitting any UV-C radiation into a room and have attempted to confine UV-C radiation to the interior of a closed (i.e., UV-C baffled) chamber, and to pass air through the baffled chamber for sterilization.

In in-duct systems, the volume of air passed through the sterilization zone may be significant where the air mover is external of the room and the size and noise of operation of the air mover is not a prime consideration. However, such systems generally circulate the contaminated air throughout the room, and often throughout several rooms, before it is drawn into the return ducts for sterilization. Moreover, the operation of in-duct systems is effective only when the HVAC system is activated and an infected person may saturate the air with germs when the system is not operating. The use of greater insulation for energy conservation results in less use of the system and less likelihood of effective sterilization.

Where the sterilization occurs in a ceiling mounted room system, the size, noise and drafts caused by the air mover are significant considerations. At acceptable levels, the volume of air moved through the sterilization zone in the upper part of the room is relatively small.

Portable floor or table standing UV-C air purifiers are used in proximity to people, pets and plants, etc. and UV-C irradiation outside of the units poses an obvious safety hazard. As a result, the sterilization is highly localized leaving pockets of contaminated air. Space heaters are a good analogy, heating the area of the room closest to the heater and re-circulating the heated air for reheating will eventually warm the area adjacent the heater to a comfortable level. However, areas not in proximity to the space heater will remain unacceptably cool.

In a few instances where the space is a small, confined area such as an elevator car, a portion of the ceiling and side walls of the car may serve as part of the surfaces that define the closed radiation chamber into which the blower forces air. Because of the small size of the elevator car, the blowers are necessarily of small size, high speed and therefore noisy. In such systems, the lower part of the blower fixture occupies almost all of the ceiling area of the space and a very small amount of radiation may be allowed to laterally radiate a few inches beyond the blower fixture. Such systems depend on the small size of the elevator car and the relatively large size of the fixture to establish the air currents necessary to pass air through the sterilization zone. Such a ratio of fixture to room is impractical for use in rooms.

Initial efforts to effect air sterilization in a room with a UV-C field external of a radiation chamber transmitted an intense UV-C beam at a room height well above the "eye level" of people occupying the room, i.e., generally considered to be approximately 6.5 feet above the floor. Germ reduction occurred in the air passing through the beam as a result of convection currents and the ventilation systems. While the intensity of the beam was effective in sterilizing the air actually passing through the beam, the volume and velocity of the air passing through the beam was not controlled and such devices have generally been effective in sterilizing only the air in the upper part of the room air and have not adequately reduced the circulation of contaminated air. In addition, the narrowing of the beam vertically, typically through the use of louvers, absorbed most of the UV-C energy within the fixture making such fixtures highly inefficient.

Experiments recently have been conducted by the Harvard University School of Public Health with high intensity UV-C sources in which the amount of room air passing through the field of UV-C radiation is increased by the use of independent air movers. Such air movers serve to stir or mix the air in the room, combining treated air with untreated air, so that mixed air is circulated back through the UV-C killing field. Experimental data suggest that such systems were roughly three times more effective in reducing the concentration of microorganisms in the room than the conventional high energy "beam" sterilizers without the use of independent air movers. See Melvin A. First, et al "Fundamental Factors Affecting Upper Room Ultraviolet Germicidal Irradiation", *Journal of Occupational and Environmental Hygiene*, May, 2007 pp. 321-331.

Applicant has proposed to combine the air sterilization and air movement features needed to effectively sterilize room air into a single ceiling paddle fan fixture. Ceiling paddle fans are quiet, efficient and high volume air mixers and are well known for use in rooms. The large slowly rotating blades are designed to move large volumes of air at a relatively slow speed, and are therefore quiet. Paddle fans create a cooling effect by causing more rapid evaporation of perspiration and are often used as a less expensive alternative (or supplement) to air conditioning. To save energy in cold months, coinciding with the flu and cold season, paddle fans are also being reversed to force heated air downwardly into the peopled space. By reversing the fan and operating at low speeds, drafts are minimal.

Ceiling paddle fans are generally mounted near the center of a room, or are spaced apart in large rooms. The blades of paddle fans are typically slanted at an angle of about 10° to 15° from the horizontal on the leading edge—i.e., when operated in a clockwise direction, the blades will cause a generally horizontal and downward flow of air in the middle of the room where it is mixed with room air and re-circulated upwardly at the room walls and drawn along the ceiling above the paddle fan. Conversely, if the blades are operated in a counterclockwise direction, air will tend to be pulled up vertically in the center of the room against the ceiling and then redistributed horizontally and ultimately downwardly where it is mixed with room air and re-circulated upwardly to the paddle fan. If used in this manner, the fans may help to redirect heated air back into the lower room which would be useful in colder months. Because of their pleasing appearance and potential to quietly circulate air and reduce energy consumption, paddle fans have been widely adopted.

Applicant's co-pending application discloses an improved ceiling paddle fan sterilization fixture that uses a low intensity source with a paddle ceiling fan to significantly increase the mixing of the treated air with the untreated room air for recirculation through the sterilization zone. Sterilization of room air is achieved by the passage of a high volume of air at a relatively slow speed through a relatively large but low intensity UV-C radiation field. Because diseases transmitted via air are very susceptible to even low intensity UV-C beams, a broad diffuse irradiation through which a large volume of air is circulated is sufficient to kill a large percentage of cold, flu, respiratory (SARS virus, e.g.) and tuberculosis cells.

Important features of the present invention are the relatively large size of the diffuse sterilization zone, the relatively low UV radiation levels, the relatively high volume of air circulated, and the ability to operate the paddle fan so as to draw contaminated air through the sterilization field prior to circulation throughout the room.

In contrast to applicant's co-pending application where the air sterilization and air movement is achieved with a single fixture, the present application is directed to a medallion for paddle ceiling fans. Decorative medallions have been used extensively to aesthetically enhance designs of paddle fans and light fixtures such as chandeliers. The present invention achieves air sterilization through the use of a decorative medallion and thus avoids unsightly and space utilization interfering intrusions commonly found in air sterilization products. In embodiments where indirect lighting is also provided in the medallion, the same results are also achieved. Because light kits now used for illumination are usually suspended below ceiling paddle fans, the greater height of medallion lighting reduces glare on computer and television screens within the room. Still further advantages are achieved through the use of fluorescent lamps in lieu of incandescent lamps commonly used in light kits; these include energy savings and lower maintenance.

While of greatest benefit with presently installed paddle ceiling fans in public spaces such as hospitals, health care institutions, dormitories, schools and offices, the present invention may be used in residential applications, being easily installed by the homeowner in association with existing or replacement paddle ceiling fans.

The present invention establishes a sterilization zone through which air circulated by the ceiling fan, convection currents, etc. While the sterilization zone may be defined in different ways, it is important for safety reasons that the radiation intensity in the peopled area outside of the zone not exceed the thresholds established by the American Council of Governmental and Industrial Hygiene (ACGIH), i.e., 0.4 microwatts per square centimeter of UV-C irradiance nor exceed total exposure above 6.0 micro joules per square centimeter over an 8 hour period.

In the preferred embodiment described herein, the amount and intensity of the UV-C radiation generated and the configuration of the fixture cover are designed to provide a diffuse sterilization zone extending downwardly from the ceiling approximately one foot and radially outward from the center of the paddle fan to a point approximately one foot beyond the blades of paddle fans. For a typical 52" diameter ceiling paddle fan suspended one foot below an 8 foot ceiling, the sterilization zone is thus a cylinder about 6' in diameter and one foot tall, i.e., approximately 28 cubic feet. Such a zone is entirely above the plane of the fan paddles and thus the rotating paddles provide an area unlikely to be peopled.

In other embodiments suitable for higher ceilings, the radius of the sterilization zone defined by a predetermined radiation intensity may be increased by higher wattage UV-C sources and/or enlargement of the slits through which the radiation escapes the medallion.

The typical paddle ceiling fan moves 1,500 cubic feet per minute on low and thus passes approximately 90,000 cubic feet of air through the sterilization zone of the preferred embodiment in an hour. In a typical 14'×14'×8' room containing approximately 1,600 cubic feet of air, the amount of air passing through the sterilization zone in an hour is over 56 times the volume of air in the room. Pockets of contaminated air are reduced by the continuous mixing of the sterilized air with contaminated room air and the concentration of germs is materially reduced before they can be circulated into other parts of the room and infect others. Compared with beam type ceiling fixtures, applicant's relatively high volume of air circulated by the ceiling paddle fan and the relatively large UV-C sterilization zone is several times more useful in reducing airborne germs.

It is accordingly an object of the present invention to provide a medallion that may be mounted on the ceiling of a room around the canopy of a ceiling paddle fan which will result in a useful reduction of germ concentration in the entire room without exposing people, pets, plants or room furnishings, ceilings or walls to potentially harmful levels UV-C.

Another object is to provide a medallion for a paddle ceiling fan that may be operated to pull air upwardly into the sterilization zone and thus immediately move recently generated germs from proximity of those generating them tending to prevent the contaminated air from being circulated to others in the room.

Still another object of the present invention is to provide a medallion that both sterilizes air and provides indirect room lighting.

Many other objects and advantages will be apparent from the following detailed description of preferred embodiments when read in conjunction with the appended drawings.

THE DRAWINGS

DETAILED DESCRIPTION OF A PREFERRED EMBODIMENTS

Figure 1:
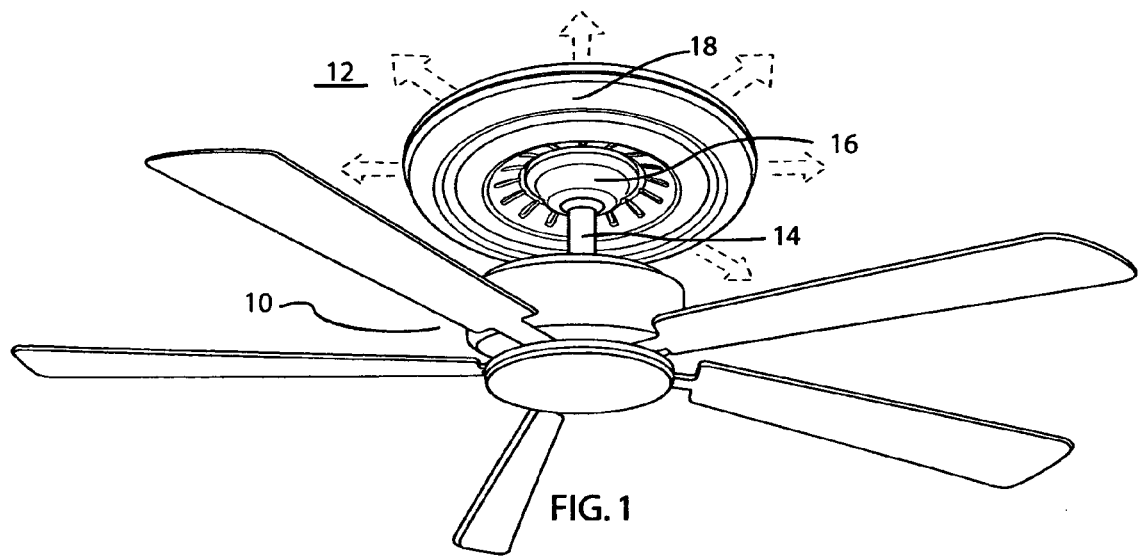
FIG. 1 is a pictorial representation of one embodiment of the medallion of the present invention.

One embodiment of the present invention is illustrated in FIG. 1. Referring to the figure, a conventional ceiling paddle fan 10 is suspended from the ceiling 12 from a canopy 16 and a rod 14. The medallion 18 of the present invention surrounds the canopy 16 and is flush mounted to the ceiling 12. As suggested by the arrows, the medallion 18 emits radiation horizontally along the ceiling 12.

Figure 2:
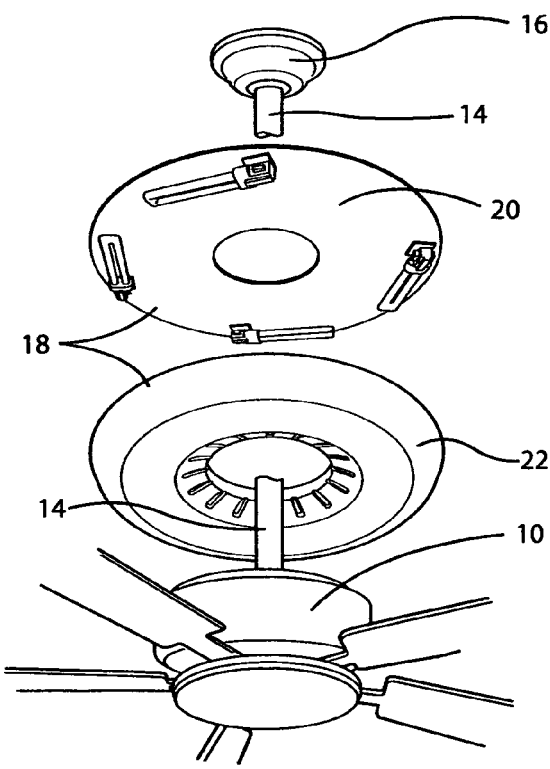
FIG. 2 is an exploded pictorial representation of the medallion of FIG. 1 showing the installation of the medallion over the canopy of a ceiling paddle fan.
Figure 3:
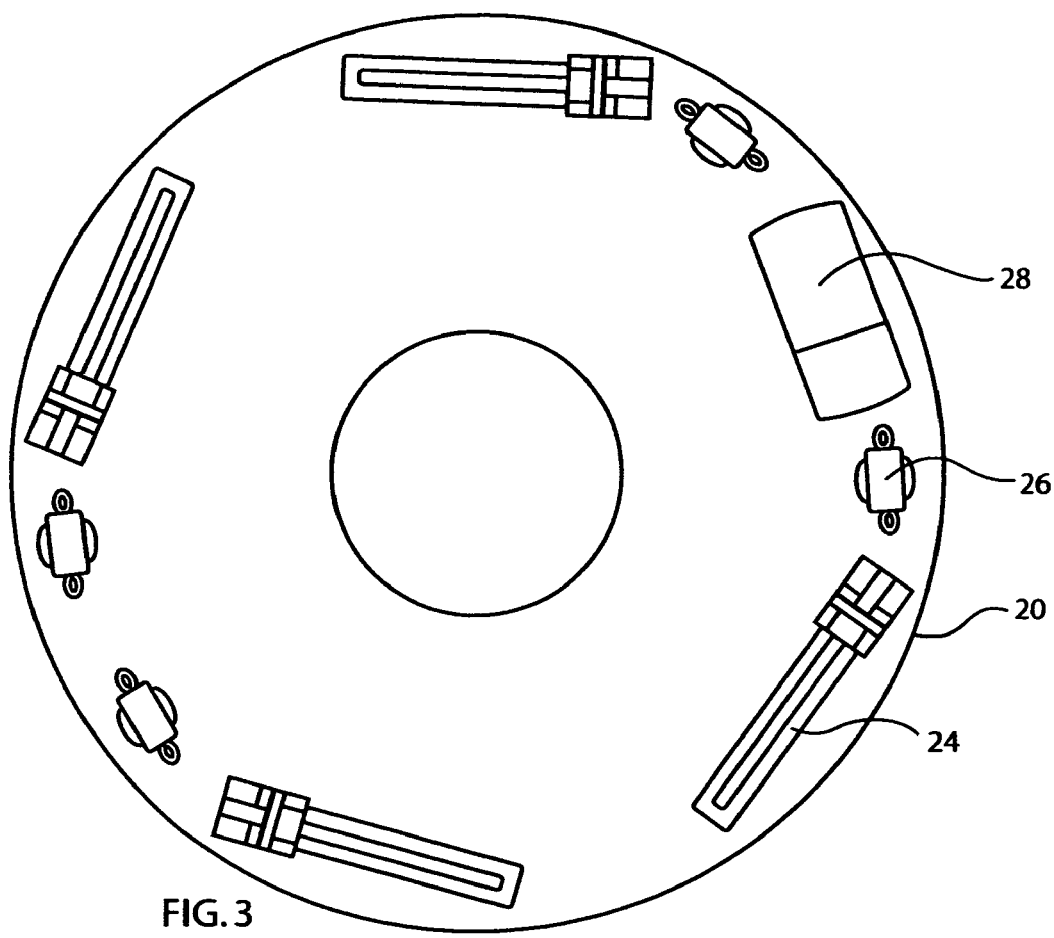
FIG. 3 is a pictorial representation of the downwardly facing side of the plate of FIG. 1 illustrating one arrangement of UV-C and visual light sources.
Figure 4:
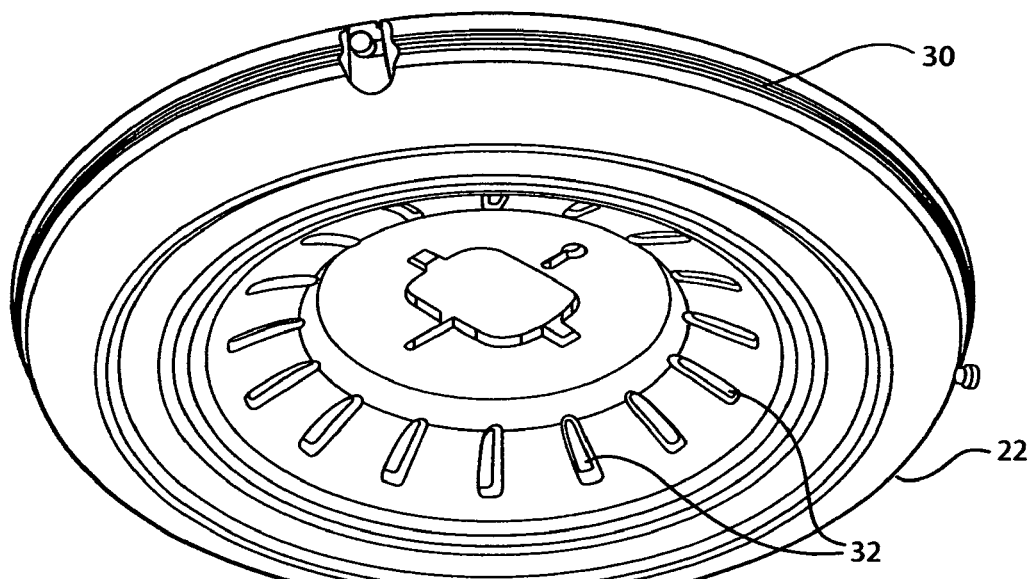
FIG. 4 is a pictorial representation showing the cover plate of the medallion of FIG. 1 showing the horizontal and radial slots.

As shown in more detail in the exploded view of FIG. 2, the medallion 18 includes a plate 20 and a cover 22. As shown in FIG. 3, the downward facing surface of the plate 20 includes one or more UV-C emitting lamps 24 with appropriate ballasts 26. The UV-C emitting lamps may be of the type illustrated or may be arcuate lamps, desirably semicircular in length and circular in cross-section. Where visible light is desired, one or more of the lamps 24 may be replaced with conventional fluorescent lamps to provide indirect room lighting. In such instances, it is desirable for the cover transmit visible light while remaining opaque to UV-C radiation, e.g. glass.

A conventional remote control device 28 may be added so that the operation of the lamps may be remotely controlled. While not shown in the interest of clarity, an UV opaque molded trim plate and ballast covers are desirably used to protect conventional insulation on wiring and ballasts.

The cover 22 is desirably molded to a visually pleasing shape out of a material opaque to UV-C radiation. The UV-C radiation from the lamps 24 exits the cover 22 in a substantially horizontal direction through one or more narrow slits 30 in the periphery of the cover 22. Radiation may also exit the cover 22 through a plurality of radially extending openings 32 near the opening for the canopy 16 in the center of the cover 22. These openings 22 may be formed to partially baffle the radiation to direct the radiation at a flat angle. An interlock switch (not shown in the interest of clarity) is used to disable the UV-C source in the event that the cover is removed.

Figure 5:
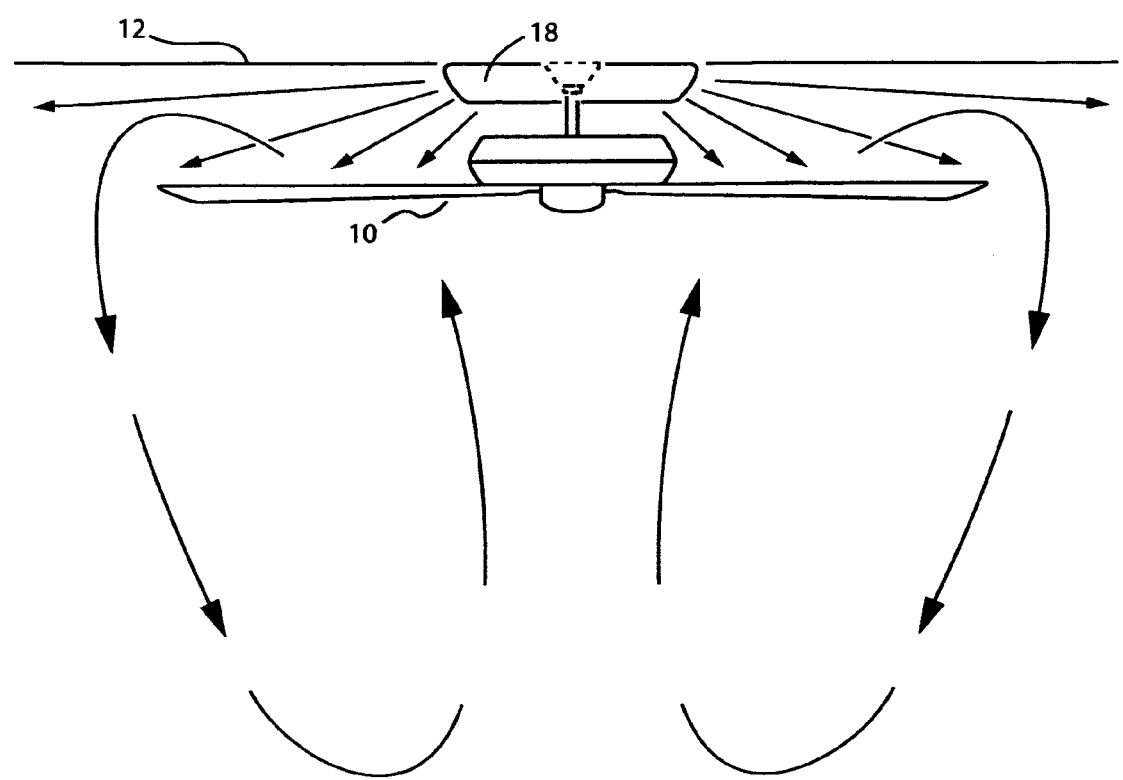
FIG. 5 is a pictorial representation showing the sterilization zone between the paddle fan and the ceiling and the circulation of air through the sterilization zone.

In operation as shown in FIG. 5, the envelope of the safe UV-C radiation, i.e., the sterilization zone, exists between the ceiling 12 and the paddle fan 10 and extends horizontally a small distance beyond the periphery of the paddle fan blades. Air from the room is drawn upwardly by the rotation of the paddle fan through sterilization zone and pushed outwardly along the ceiling 12 from whence it circulates downwardly into the room, mixing with room air and re-circulating through the sterilization zone.

Reversal of the direction of rotation of the paddle fan blades will reverse the air circulation shown drawing air inwardly along the ceiling through the sterilization zone and pushing the sterilized air downwardly beneath the paddle fan.

The velocity of air created by the fan is highest at the center of the fan so that more air flows through the most intense area of the sterilization zone immediately above the fan. Some air flows through the medallion itself via the apertures therein.

Direct UV radiation intensity declines exponentially with distance and is a function of the power and efficiency of the source and the materials through which the radiation must pass. UV radiation also diffuses and this is a function of the size of the openings in the cover. The "sterilization zone" is defined herein as the volume of space in which the threshold recommended by the American Council of Governmental and Industrial Hygiene (ACGIH) threshold standard of 0.4 $\gamma w/cm^2$ is not exceeded. In the preferred embodiment, the UV-C sources are activated only when the paddle fan is operating and the radiation zone is horizontally limited to the proximity of the paddle fan blades so that a person's avoidance of the spinning blades places such person at the edge of the radiation zone. The same effect is achieved vertically in the preferred embodiment by vertically limiting the radiation zone to within 12" of the ceiling or to a plane above the plane of the paddle fan blades.

While the foregoing is a description of preferred embodiments, many variations and modifications will naturally occur to those of skill in this art from a perusal hereof. The invention is therefore not to be limited to the embodiments disclosed, but defined only by the claims when accorded a full range of equivalents.

What is claimed is:

1. A medallion in-room air sterilizer for use with a ceiling paddle fan supported by a hollow rod extending from a ceiling canopy comprising:
   a UV-C opaque decorative housing configured to be positioned against the ceiling of a room around said canopy and fan supporting hollow rod; and
   a source of UV-C radiation operatively mounted within said housing, the horizontal periphery of said housing being apertured to permit direct UV-C radiation to radiate therefrom in a substantially horizontal direction and a downward facing surface of said housing being apertured to permit indirect UV-C radiation to radiate downwardly therefrom to thereby create a sterilization zone immediately above the paddle fan between the room ceiling and the plane of the fan paddles without providing a radiation intensity greater than a predetermined value outside of said sterilization zone.

2. The medallion of claim 1 wherein said UV-C source is operable only when the fan is operating.

3. The medallion of claim 1 wherein said housing includes a receiver responsive to a remote signal for controlling the operation of said UV-C source.

4. The medallion of claim 1 wherein said housing includes a motion detector for controlling the operation of said UV-C source.

5. The medallion of claim 1 wherein said housing includes a source of visual light.

6. The medallion of claim 5 wherein said visual light source is fluorescent.

7. The medallion of claim 1 wherein said sterilization zone extends no more than ten inches below the ceiling against which the medallion is positioned.

8. The medallion of claim 1 wherein said sterilization zone does not extend downwardly within 6.5 feet of the floor of the room in which the medallion is mounted.

9. The medallion of claim 1 wherein said value is 0.4 microwatts per square centimeter.

10. The medallion of claim 1 wherein said value is 6.0 microJoules per square centimeter over an 8 hour period.

11. In combination, a ceiling paddle fan supported by a hollow rod extending from a ceiling canopy and a medallion, said medallion comprising:
   a UV-C decorative housing configured to be positioned against the ceiling of a room around said canopy and fan supporting hollow rod; and a source of UV-C radiation operatively mounted within said housing for providing UV-C radiation in a substantially horizontal direction and in a downward direction to thereby create a UV-C radiation zone immediately above the paddle fan between the room ceiling and the plane of the fan paddles.

12. The medallion of claim 11 where the radiation includes visible light.

13. The medallion of claim 11 where the source of radiation is fluorescent.

14. In combination within a room having a floor and a ceiling spaced apart a distance not less than about 8 feet, a ceiling paddle fan suspended from said ceiling by a canopy and a hollow rod and a medallion, said medallion comprising:
- a UV-C opaque decorative housing configured to be positioned against said ceiling around said canopy and said hollow rod; and
- a source of UV-C radiation operatively mounted within said housing, the horizontal periphery of said housing being apertured to permit direct UV-C radiation to radiate therefrom in a substantially horizontal direction and a downward facing surface of said housing being apertured to permit indirect UV-C radiation to radiate downwardly therefrom to thereby create a sterilization zone immediately above said paddle fan between said ceiling and the plane of the fan paddles without providing a radiation intensity greater than a predetermined value outside of said sterilization zone.

15. In combination within a room having a floor and a ceiling spaced apart a distance not less than about 8 feet, a ceiling paddle fan suspended from said ceiling by a canopy and a hollow rod and a medallion, said medallion comprising:
- a UV-C opaque decorative housing configured to be positioned against said ceiling around said canopy and said hollow rod; and
- a source of UV-C radiation operatively mounted within said housing to radiate therefrom in a substantially horizontal direction and in a downward facing direction to thereby create a UV-C radiation zone immediately above said paddle fan between said ceiling and the plane of the fan paddles.

16. The combination of claim 15 wherein said source is fluorescent.

17. The medallion of claim 1 wherein the radial extent of said zone is greater than two times the length of the fan paddles.

18. The medallion of claim 17 wherein the radial extent of said zone is greater than two and less than four times the length of the fan paddles.

* * * * *